US006603024B1

United States Patent
Harada et al.

(10) Patent No.: US 6,603,024 B1
(45) Date of Patent: Aug. 5, 2003

(54) PROCESS FOR THE PREPARATION OF 3,4-METHYLENEDIOXYMANDELIC ACID

(75) Inventors: Katsumasa Harada, Ube (JP); Masashi Shirai, Ube (JP); Koji Shiba, Ube (JP)

(73) Assignee: Ube Industries, Ltd., Ube (JP)

( * ) Notice: Subject to any disclaimer, the term of this patent is extended or adjusted under 35 U.S.C. 154(b) by 4 days.

(21) Appl. No.: 10/110,263

(22) PCT Filed: Oct. 13, 2000

(86) PCT No.: PCT/JP00/07103

§ 371 (c)(1),
(2), (4) Date: Apr. 2, 2002

(87) PCT Pub. No.: WO01/27100

PCT Pub. Date: Apr. 19, 2001

(30) Foreign Application Priority Data

Oct. 13, 1999 (JP) .......................................... 11-290774
Nov. 16, 1999 (JP) .......................................... 11-326116

(51) Int. Cl.[7] ...................... C07D 323/02; C07D 317/44
(52) U.S. Cl. ........................................ 549/434; 549/445
(58) Field of Search ................................. 549/445, 434

(56) References Cited

U.S. PATENT DOCUMENTS 4,190,583 A  2/1980  Bauer et al.

FOREIGN PATENT DOCUMENTS

| EP | 0 002 460 A1 | 6/1979 |
| JP | 54-95573 A | 7/1979 |
| JP | 8-59650 A | 3/1996 |

OTHER PUBLICATIONS

Libor Cerveny et al., *Perfumer & Flavorist*, "Synthesis of Heliotropin", vol. 14, Mar./Apr. 1989, pp. 13–18.

*Primary Examiner*—Amelia Owens
(74) *Attorney, Agent, or Firm*—Frishauf, Holtz, Goodman & Chick, P.C.

(57) ABSTRACT

A process for preparing 3,4-methylenedioxymandelic acid by reacting 1,2-methylenedioxybenzene with glyoxylic acid in the presence of a strong acid and of at least one substance selected from the group consisting of an aprotic organic solvent and 100 to 1200 ml of an organic acid per kg of 1,2-methylenedioxybenzene.

25 Claims, 1 Drawing Sheet

PROCESS FOR THE PREPARATION OF 3,4-METHYLENEDIOXYMANDELIC ACID

CROSS REFERENCE TO RELATED APPLICATION

This application is a U.S. National Phase Application under 35 U.S.C. 371 of International Application No. PCT/JP00/07103 filed Oct. 13, 2000.

TECHNICAL FIELD

The present invention relates to a process for preparing 3,4-methylenedioxymandelic acid from 1,2-methylenedioxybenzene. 3,4-Methylenedioxymandelic acid is a useful compound as a starting material for synthesis of medicines, agrochemicals, and the like, and as a starting material for heliotropin used as general cosmetics and perfumes.

BACKGROUND ART

A process for preparing 3,4-methylenedioxymandelic acid by reacting 1,2-methylenedioxybenzene with glyoxylic acid in the presence of a strong acid such as sulfuric acid or phosphoric acid has already been known (for example, Japanese Provisional Patent Publication No. 95573/1979 which corresponds to U.S. Pat. No. 4,190,583, Perfumer & Flavourist, vol. 14, p. 13 (1989)). In the process described above, however, the product 3,4-methylenedioxymandelic acid is insoluble in this reaction system and thus precipitated as crystals and, as the reaction proceeds, the reaction solution is made highly viscous or solidified to make stirring very difficult. Another problem is that this reaction is an exothermic reaction, so that when the reaction solution is made highly viscous or solidified, the whole of the reaction solution is hardly cooled, and the temperature of the solution is partially increased to cause formation of byproducts, thus reducing the selectivity of 3,4-methylenedioxymandelic acid. In particular, this phenomenon occurs significantly when the reaction is in a large scale.

Japanese Provisional Patent Publication No. 95573/1979 supra describes that the reaction is carried out preferably in the absence of a solvent, and if necessary, addition of formic acid or acetic acid exerts an advantageous influence on the reaction. Thus, the type and effect of solvent are not described, and when an organic acid is used, the specific amount of the organic acid added is not described either. Accordingly, we made extensive study on this reaction and found that the problem described above can be solved by adding an organic solvent. Further, we unexpectedly found that when an organic acid is used, the formation rate and selectivity of 3,4-methylenedioxymandelic acid are significantly influenced by the amount of the organic acid added to 1,2-methylenedioxybenzene, and that there is the optimum amount of the organic acid added.

An object of this invention is to provide an industrially preferable process for preparing 3,4-methylenedioxymandelic acid, which can produce 3,4-methylenedioxymandelic acid in high selectivity by reacting 1,2-methylenedioxybenzene with glyoxylic acid and which can also be applied to the reaction in a large scale.

SUMMARY OF THE INVENTION

The present invention relates to a process for preparing 3,4-methylenedioxymandelic acid by reacting 1,2-methylenedioxybenzene with glyoxylic acid in the presence of a strong acid, characterized in that the reaction is carried out in the presence of at least one selected from the group consisting of an aprotic organic solvent and 100 to 1200 ml of an organic acid per kg of 1,2-methylenedioxybenzene.

BEST MODE FOR CARRYING OUT THE INVENTION

Figure 1:
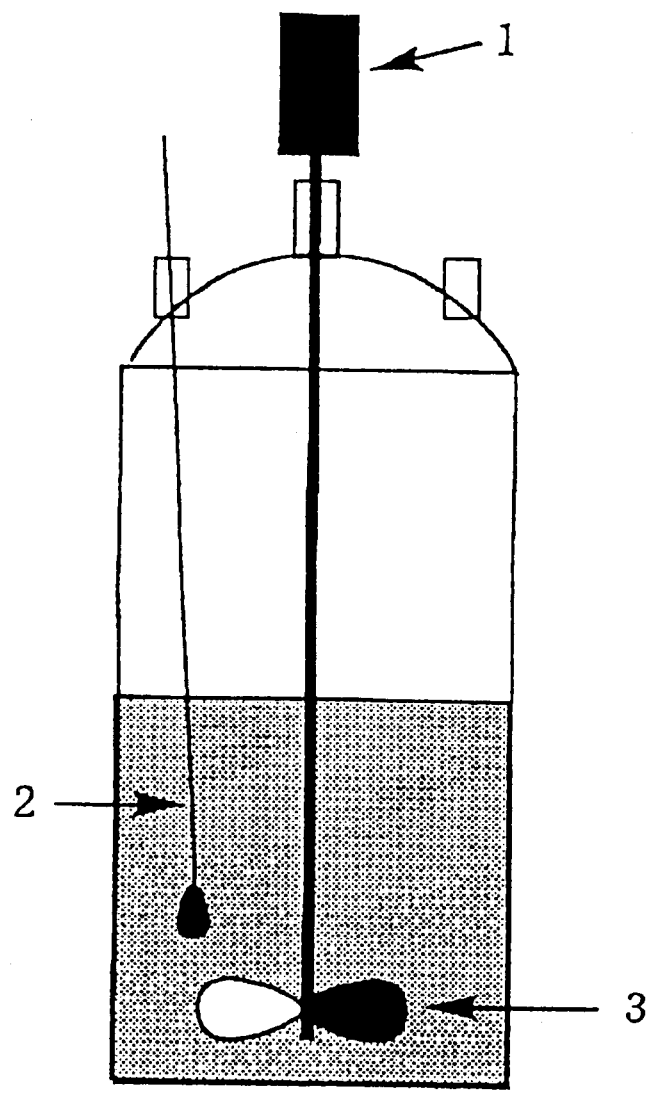
FIG. 1 is a drawing showing one example of a reaction apparatus used in a process of the present invention.

The strong acid used in the reaction of the present invention includes inorganic acids such as sulfuric acid and phosphoric acid, and organic acids having a pKa of 3 or less such as methanesulfonic acid, and preferably an inorganic acid, more preferably sulfuric acid is used. These strong acids are used in the form of 70% by weight or more aqueous solution. The amount of the strong acid used is preferably 0.50 to 3.00 mol, more preferably 1.00 to 2.50 mol, per mol of 1,2-methylenedioxybenzene.

Glyoxylic acid used in the reaction of the invention can be used not only in the form of solid (monohydrate) but also in the form of 40% by weight or more aqueous solution. The amount of glyoxylic acid used is preferably 0.8 to 3.0 mol, more preferably 1.0 to 2.0 mol, per mol of 1,2-methylenedioxybenzene.

The aprotic organic solvent used in the reaction of the present invention is not particularly limited insofar as it is stable under acidic conditions and does not inhibit the reaction, and examples thereof include ethers such as diethyl ether, diisopropyl ether, dibutyl ether and tetrahydrofuran; ketones such as acetone, 2-butanone, 2-pentanone, 3-pentanone, 4-methyl-2-pentanone, cyclopentanone and cyclohexanone; carboxylic acid esters such as ethyl formate, isopropyl formate, butyl formate, methyl acetate, ethyl acetate, isopropyl acetate, butyl acetate, methyl propionate, ethyl propionate, isopropyl propionate and butyl propionate; amides such as N,N-dimethylformamide, N,N-dimethylacetamide, hexamethyl phosphoric triamide and 1-methyl-2-pyrrolidone; urea or analogues thereof such as 1,3-dimethyl-2-imidazolidone; carbonic acid esters such as dimethyl carbonate and diethyl carbonate; and sulfoxides such as dimethyl sulfoxide.

The amount of the aprotic organic solvent used is preferably 100 to 2000 ml, more preferably 100 to 1000 ml, per kg of 1,2-methylenedioxybenzene. These organic solvents may be used singly or in combination thereof.

The organic acid used in the reaction of the present invention is not particularly limited insofar as it is stable under acidic conditions and does not inhibit the reaction, and examples thereof include aliphatic carboxylic acids such as formic acid, acetic acid, propionic acid, n-butyric acid, isobutyric acid and n-valeric acid; and halogenated aliphatic carboxylic acids such as trifluoroacetic acid and dichloroacetic acid, and preferably an aliphatic carboxylic acid, more preferably acetic acid is used. These organic acids may be used singly or in combination thereof.

The amount of the organic acid used is 100 to 1200 ml, preferably 100 to 1000 ml and more preferably 100 to 500 ml, per kg of 1,2-methylenedioxybenzene. When the amount of the organic acid used is less than 100 ml, there is the problem that the ability of the reaction solution to be stirred is significantly worsened, and the temperature of the solution is partially increased to cause formation of byproducts, thus reducing the selectivity of the desired product, while if the amount of the organic acid is greater than 1200 ml, there is the problem that the reaction rate is significantly reduced, the reaction requires a longer time, and the selectivity of the desired product is lowered.

The reaction of this invention is carried out, for example, according to a method of adding glyoxylic acid and a strong acid to a mixture of 1,2-methylenedioxybenzene and an aprotic organic solvent and/or an organic acid (100 to 1200 ml per kg of 1,2-methylenedioxybenzene) in an atmosphere of an inert gas such as nitrogen or argon. The reaction temperature at this time is preferably −20 to 10° C., more preferably −10 to 5° C. The reaction is carried out at normal pressure but may also be carried out under pressure or under reduced pressure if necessary. The reaction time is usually 1 to 100 hours, preferably about 3 to 75 hours.

After the reaction is finished, the resulting product is neutralized by adding, e.g., a suitable amount of a base, then, extracted with a suitable solvent, separated and purified by general techniques such as column chromatography, distillation and recrystallization.

EXAMPLES

Next, the present invention is described in more detail by reference to the Examples, which are not intended to limit the scope of the present invention. Incidentally, the selectivity of 3,4-methylenedioxymandelic acid formed was calculated on the basis of the amount (in terms of moles) of 1,2-methylenedioxybenzene consumed.

Example 1

A flat bottom separable flask with an internal volume of 500 ml as shown in FIG. 1 was charged with 50.0 g (0.409 mol) of 1,2-methylenedioxybenzene and 25 ml of 4-methyl-2-pentanone (the amount of the organic solvent used was 500 ml per kg of 1,2-methylenedioxybenzene) in a nitrogen atmosphere, and the mixture was cooled to −5° C. with stirring. In FIG. 1, the reference numeral 1 denotes a motor, 2 denotes a thermometer, and 3 denotes a stirring blade, respectively. Then, a mixture of 83.4 g (0.450 mol) of a 40% by weight aqueous glyoxylic acid solution and 85.8 g (0.839 mol) of 96% by weight sulfuric acid was added dropwise thereto, and the mixture was stirred at −5° C. for 21 hours. Incidentally, the mixture could be stirred smoothly during the reaction.

Thereafter, the reaction solution was neutralized by adding 102.0 g (1.67 mol) of 28% by weight aqueous ammonia little by little. Then, 100 ml of 2-butanone was added, then the mixture was heated to 60° C., and the formed 3,4-methylenedioxymandelic acid was extracted into a 2-butanone layer (an organic layer). Analysis of the organic layer by high performance liquid chromatography indicated that the conversion of 1,2-methylenedioxybenzene was 95%, and the selectivity of 3,4-methylenedioxymandelic acid was 92%.

Examples 2 to 4

The reaction was carried out in the same manner as in ample 1 except that the organic solvent used, the action temperature and the reaction time in Example 1 were changed. The results are shown in Table 1.

TABLE 1

| Example | Aprotic organic solvent | Reaction temperature (° C.) | Reaction time (h) | MDB Conversion (%) | MDMA Selectivity (%) |
| --- | --- | --- | --- | --- | --- |
| 2 | 3-Pentanone | −5 | 23 | 94 | 91 |
| 3 | Dimethyl carbonate | 0 | 28 | 93 | 91 |
| 4 | Acetonitrile | 0 | 45 | 87 | 92 |

MDB: 1,2-Methylenedioxybenzene
MDMA: 3,4-Methylenedioxymandleic acid

Comparative Example 1

The reaction was carried out in the same manner as in Example 2 except that the organic solvent in Example 2 was not added. The reaction solution was made highly viscous during the reaction to permit only a part of the solution around the stirring blade to be stirred, thus failing to sufficiently stir the whole of the solution. As a result, the conversion of 1,2-methylenedioxybenzene was 94%, and the selectivity of 3,4-methylenedioxymandelic acid was 77%.

Example 5

A flat bottom separable flask with an internal volume of 7 L as shown in FIG. 1 was charged with 500.0 g (4.09 mol) of 1,2-methylenedioxybenzene and 250 ml of 4-methyl-2-pentanone (the amount of the organic solvent used was 500 ml per kg of 1,2-methylenedioxybenzene) in a nitrogen atmosphere, and the mixture was cooled to −10° C. with stirring. Then, a mixture of 833.7 g (4.05 mol) of 40% by weight aqueous glyoxylic acid and 857.5 g (8.39 mol) of 96% by weight sulfuric acid was added slowly dropwise thereto, and the mixture was stirred at −5° C. for 23 hours. Incidentally, the mixture could be stirred smoothly during the reaction.

Thereafter, the reaction solution was neutralized by adding 1030.0 g (16.93 mol) of 28% by weight aqueous ammonia little by little. Then, 3000 ml of 4-methyl-2-pentanone was added, then the mixture was heated to 80° C., and the formed 3,4-methylenedioxymandelic acid was extracted into a 4-methyl-2-pentanone layer (an organic layer). Analysis of the organic layer by high performance liquid chromatography indicated that the conversion of 1,2-methylenedioxybenzene was 95%, and the selectivity of 3,4-methylenedioxymandelic acid was 90%.

Example 6

A flat bottom separable flask with an internal volume of 500 ml was charged with 50.0 g (0.409 mol) of 1,2-methylenedioxybenzene and 20 ml of acetic acid (the amount of acetic acid used was 400 ml per kg of 1,2-methylenedioxybenzene) in a nitrogen atmosphere, and the mixture was cooled to 0° C. with stirring. Then, a mixture of 83.4 g (0.450 mol) of 40% by weight aqueous glyoxylic acid solution and 85.8 g (0.839 mol) of 96% by weight sulfuric acid was added dropwise thereto, and the mixture was stirred at 0° C. for 9 hours. Incidentally, the mixture could be stirred smoothly during the reaction.

Thereafter, the reaction solution was neutralized by adding 102.0 g (1.68 mol) of 28% by weight aqueous ammonia little by little. Then, 100 ml of 2-butanone was added, then the mixture was heated to 60° C., and the formed 3,4-methylenedioxymandelic acid was extracted into a 2-butanone layer (an organic layer). Analysis of the organic layer by high performance liquid chromatography indicated that the conversion of 1,2-methylenedioxybenzene was 95%, and the selectivity of 3,4-methylenedioxymandelic acid was 91%.

Examples 7 to 12

The reaction was carried out in the same manner as in Example 6 except that the amount of acetic acid used for 1,2-methylenedioxybenzene, the reaction temperature and the reaction time in Example 6 were changed. The results are shown in Table 2.

Comparative Examples 2 to 3

The reaction was carried out in the same manner as in Example 6 except that the amount of acetic acid used for 1,2-methylenedioxybenzene was outside the scope of the present invention, and the reaction temperature and the reaction time in Example 6 were changed. The results are also shown in Table 2.

TABLE 2

| Example and Comparative example | Amount of Acetic acid[1) (ml/kg) | Reaction temperature (° C.) | Reaction time (h) | MDB Conversion (%) | MDMA Selectivity (%) |
|---|---|---|---|---|---|
| Example 7 | 100 | 0 | 5 | 93 | 91 |
| Example 8 | 200 | 0 | 7 | 96 | 91 |
| Example 9 | 300 | 0 | 7 | 94 | 90 |
| Example 10 | 500 | 0 | 12 | 95 | 90 |
| Example 11 | 800 | 0 | 21 | 97 | 90 |
| Example 12 | 1000 | 0 | 45 | 96 | 92 |
| Comparative example 2 | 50 | 0 | 7 | 95 | 82 |
| Comparative example 3 | 1500 | 0 | 63 | 97 | 85 |

[1)An amount of acetic acid used relative to 1,2-methylene-dioxybenzene
MDB: 1,2-Methylenedioxybenzene
MDMA: 3,4-Methylenedioxymandleic acid Industrial Applicability According to the present invention, there can be provided an industrially preferable process for preparing 3,4-methylenedioxymandelic acid, which can produce 3,4-methylenedioxymandelic acid in high selectivity by reacting 1,2-methylenedioxybenzene with glyoxylic acid and which can be also applied to the reaction in a large scale.

What is claimed is:

1. A process for preparing 3,4-methylenedioxymandelic acid comprising reacting 1,2-methylenedioxybenzene with glyoxylic acid in the presence of a strong acid and in the presence of at least one aprotic organic solvent selected from the group consisting of an ether, a ketone, a carboxylic acid ester, an amide, a urea and a carbonic acid ester.

2. The process for preparing 3,4-methylenedioxymandelic acid according to claim 1, wherein the strong acid is sulfuric acid.

3. The process for preparing 3,4-methylenedioxymandelic acid according to claim 1, wherein an amount of the strong acid to be used is 0.50 to 3.00 mol per mol of 1,2-methylenedioxybenzene.

4. The process for preparing 3,4-methylenedioxymandelic acid according to claim 1, wherein an amount of the strong acid to be used is 1.00 to 2.50 mol per mol of 1,2-methylenedioxybenzene.

5. The process for preparing 3,4-methylenedioxymandelic acid according to claim 1, wherein an amount of the glyoxylic acid to be used is 0.8 to 3.0 mol per mol of 1,2-methylenedioxybenzene.

6. The process for preparing 3,4-methylenedioxymandelic acid according to claim 1, wherein an amount of the glyoxylic acid to be used is 1.0 to 2.0 mol per mol of 1,2-methylenedioxybenzene.

7. The process for preparing 3,4-methylenedioxymandelic acid according to any one of claims 1 to 6, wherein the aprotic organic solvent is at least one selected from the group consisting of diethyl ether, diisopropyl ether, dibutyl ether, tetrahydrofuran, acetone, 2-butanone, 2-pentanone, 3-pentanone, 4-methyl-2-pentanone, cyclopentanone, cyclohexanone, ethyl formate, isopropyl formate, butyl formate, methyl acetate, ethyl acetate, isopropyl acetate, butyl acetate, methyl propionate, ethyl propionate, isopropyl propionate, butyl propionate, N,N-dimethylformamide, N,N-dimethylacetamide, hexamethyl phosphoric triamide, 1-methyl-2-pyrrolidone, 1,3-dimethyl-2-imidazolidone, dimethyl carbonate, diethyl carbonate and dimethyl sulfoxide.

8. The process for preparing 3,4-methylenedioxymandelic acid according to any one of claims 1 to 6, wherein the aprotic organic solvent is used in an amount of 10 to 2000 ml per kg of 1,2-methylenedioxybenzene.

9. The process for preparing 3,4-methylenedioxymandelic acid according to any one of claims 1 to 6, wherein the aprotic organic solvent is used in an amount of 100 to 1000 ml per kg of 1,2-methylenedioxybenzene.

10. The process for preparing 3,4-methylenedioxymandelic acid according to any one of claims 1 to 6, wherein the reaction is carried out at a reaction temperature of −20 to 10° C.

11. The process for preparing 3,4-methylenedioxymandelic acid according to claim 1, wherein the aprotic organic solvent is used in an amount of 100 to 2000 ml per kg of 1,2-methylenedioxybenzene.

12. The process for preparing 3,4-methylenedioxymandelic acid according to claim 8, wherein the aprotic organic solvent is used in an amount of 100 to 2000 ml per kg of 1,2-methylenedioxybenzene.

13. The process for preparing 3,4-methylenedioxymandelic acid according to claim 1, wherein the aprotic organic solvent is used in an amount of 100 to 1000 ml per kg of 1,2-methylenedioxybenzene.

14. The process for preparing 3,4-methylenedioxymandelic acid according to claim 8, wherein the aprotic organic solvent is used in an amount of 100 to 1000 ml per kg of 1,2-methylenedioxybenzene.

15. The process for preparing 3,4-methylenedioxymandelic acid according to claim 1, wherein the reaction is carried out at a reaction temperature of −20 to 10° C.

16. The process for preparing 3,4-methylenedioxymandelic acid according to claim 7, wherein the reaction is carried out at a reaction temperature of −20 to 10° C.

17. The process for preparing 3,4-methylenedioxymandelic acid according to claim 8, wherein the reaction is carried out at a reaction temperature of −20 to 10° C.

18. The process for preparing 3,4-methylenedioxymandelic acid according to claim 9, wherein the reaction is carried out at a reaction temperature of −20 to 10° C.

19. The process for preparing 3,4-methylenedioxymandelic acid according to claim 1, wherein the aprotic organic solvent is 3-pentanone.

20. The process for preparing 3,4-methylenedioxymandelic acid according to claim 1, wherein the aprotic organic solvent is an ether.

21. The process for preparing 3,4-methylenedioxymandelic acid according to claim 1, wherein the aprotic organic solvent is a ketone.

22. The process for preparing 3,4-methylenedioxymandelic acid according to claim 1, wherein the aprotic organic solvent is a carboxylic acid ester.

23. The process for preparing 3,4-methylenedioxymandelic acid according to claim 1, wherein the aprotic organic solvent is an amide.

24. The process for preparing 3,4-methylenedioxymandelic acid according to claim 1, wherein the aprotic organic solvent is a urea.

25. The process for preparing 3,4-methylenedioxymandelic acid according to claim 1, wherein the aprotic organic solvent is a carbonic acid ester.

* * * * *